US012788352B2

(12) United States Patent
Yokoyama

(10) Patent No.: US 12,788,352 B2
(45) Date of Patent: Nov. 10, 2026

(54) RADIATION IMAGING APPARATUS, RADIATION IMAGING SYSTEM, METHOD FOR PROCESSING INFORMATION, AND STORAGE MEDIUM

(71) Applicant: CANON KABUSHIKI KAISHA, Tokyo (JP)

(72) Inventor: Keigo Yokoyama, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 229 days.

(21) Appl. No.: 18/615,466

(22) Filed: Mar. 25, 2024

(65) Prior Publication Data

US 2024/0324982 A1 Oct. 3, 2024

(30) Foreign Application Priority Data

Mar. 27, 2023 (JP) ................................ 2023-050410

(51) Int. Cl.

| | |
|---|---|
| ***A61B 6/00*** | (2024.01) |
| ***A61B 6/46*** | (2024.01) |
| ***G01C 17/38*** | (2006.01) |

(52) U.S. Cl.

CPC .............. *A61B 6/547* (2013.01); *A61B 6/461* (2013.01); *G01C 17/38* (2013.01)

(58) Field of Classification Search

CPC .......... A61B 6/587; A61B 6/585; A61B 6/582

See application file for complete search history.

(56) References Cited

U.S. PATENT DOCUMENTS

2020/0170608 A1* 6/2020 Makino ................ A61B 6/4405
2022/0183650 A1* 6/2022 Saito .................... A61B 6/4283

FOREIGN PATENT DOCUMENTS

JP 2022093760 A 6/2022

* cited by examiner

*Primary Examiner* — Dani Fox

(74) *Attorney, Agent, or Firm* — Canon U.S.A., Inc. IP Division

(57) ABSTRACT

An information processing apparatus includes one or more memories and one or more processors. The one or more memories and the one or more processors are configured to, based on a data group that is acquired in a state in which a detection unit configured to detect an orientation is not attached to a radiation imaging apparatus and is acquired by the detection unit detecting a plurality of orientations, correct an orientation that is detected by the detection unit after the plurality of orientations is detected and is acquired in a state in which the detection unit is attached to the radiation imaging apparatus.

12 Claims, 9 Drawing Sheets

BLOCK DIAGRAM OF RADIATION IMAGING SYSTEM

SCHEMATIC CONFIGURATION OF RADIATION IMAGING SYSTEM

BLOCK DIAGRAM OF RADIATION IMAGING SYSTEM

DIAGRAM OF PLOTTED DETECTION RESULTS

DIAGRAM OF DATA GROUP (P) APPROXIMATED TO ELLIPSOID

RADIATION IMAGING APPARATUS, RADIATION IMAGING SYSTEM, METHOD FOR PROCESSING INFORMATION, AND STORAGE MEDIUM

BACKGROUND

Field of the Disclosure

The present disclosure relates to a radiation imaging apparatus, a radiation imaging system, a method for processing information, and a storage medium.

Description of the Related Art

In imaging using radiation at medical sites, it is required to capture images suitable for diagnoses.

According to Japanese Patent Application Laid-Open No. 2022-93760, it is discussed that the irradiation axis of a radiation generating apparatus needs to be orthogonal to the imaging surface of a radiation imaging apparatus. According to Japanese Patent Application Laid-Open No. 2022-93760, it is discussed that a user, such as a radiological technician, adjusts the inclination of the radiation generating apparatus or the radiation imaging apparatus before imaging in order to make the irradiation axis orthogonal to the imaging plane. Further, according to Japanese Patent Application Laid-Open No. 2022-93760, it is discussed that in order to support the user in adjusting the inclination, the radiation imaging apparatus is provided with an angle detection unit, and a method is used of detecting the inclination of the radiation imaging apparatus with respect to the radiation generating apparatus, which is acquired using the angle detection unit, and displaying the inclination on a monitor. Further, according to Japanese Patent Application Laid-Open No. 2022-93760, it is discussed that a sensor that detects the gravitational acceleration (an acceleration sensor), a sensor that detects an angular velocity (a gyro sensor), and a sensor that detects an azimuth (north, south, east, and west) can be used as the angle detection means.

As an example of a sensor that detects an azimuth (north, south, east, and west), there is known a geomagnetic sensor. It is known that the geomagnetic sensor is easily affected by its ambient magnetic field (refers to a magnetic field from a magnetized reinforcing bar and a magnetic field generated from an electronic device). Thus, for example, an ambient magnetic field in imaging using radiation at a medical site can reduce the detection accuracy of the inclination of a radiation imaging apparatus with respect to a radiation generating apparatus.

SUMMARY

Embodiments of the present disclosure are directed to improving the detection accuracy of the inclination between a radiation generating apparatus and a radiation imaging apparatus.

According to an aspect of the disclosure, an information processing apparatus includes one or more memories and one or more processors. The one or more memories and the one or more processors are configured to, based on a data group that is acquired in a state in which a detection unit configured to detect an orientation is not attached to a radiation imaging apparatus and is acquired by the detection unit detecting a plurality of orientations, correct an orientation that is detected by the detection unit after the plurality of orientations is detected and is acquired in a state in which the detection unit is attached to the radiation imaging apparatus.

Further features of various embodiments of the present disclosure will become apparent from the following description of exemplary embodiments with reference to the attached drawings.

DESCRIPTION OF THE EMBODIMENTS

A radiation imaging system according to a first exemplary embodiment will be described with reference to FIGS. 1 and 2.

Figure 1:
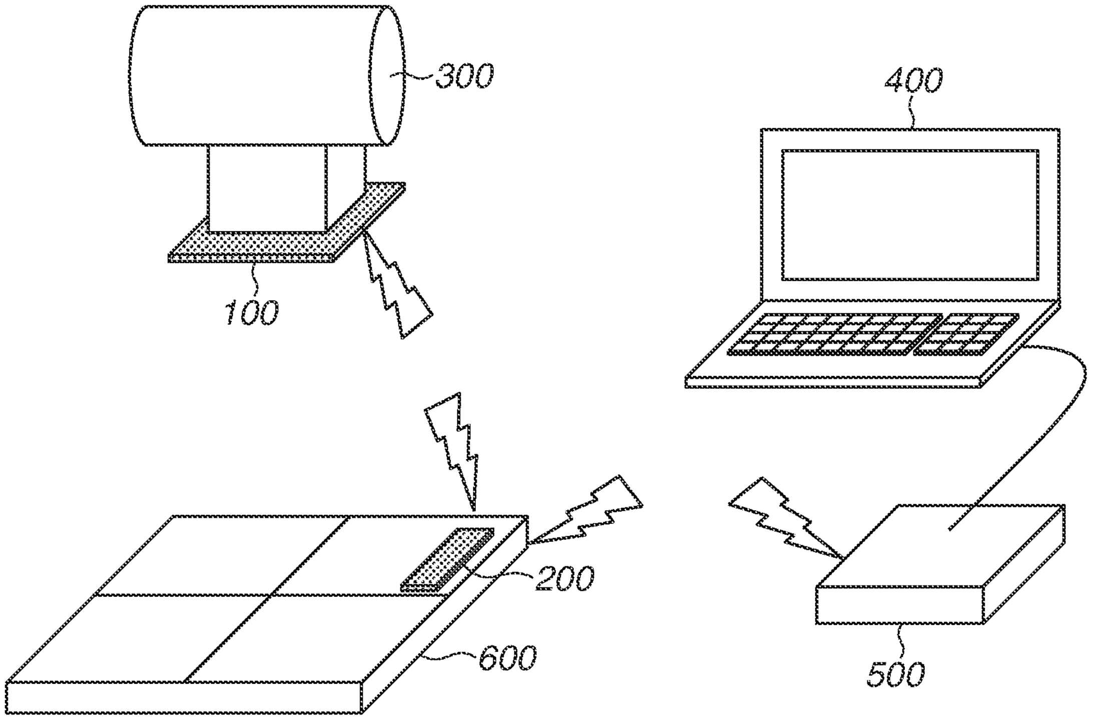
FIG. 1 illustrates a schematic configuration of a radiation imaging system.

FIG. 1 illustrates a schematic configuration of the radiation imaging system.

The radiation imaging system according to the present exemplary embodiment includes a radiation generating apparatus 300 including an X-ray tube, a detection unit 100, a radiation imaging apparatus 600 including a flat panel detector (FPD), a detection unit 200, a wireless access point 500, and an information terminal 400. The radiation generating apparatus 300 is an example of a radiation generating apparatus that generates radiation. The radiation imaging apparatus 600 is an example of a radiation imaging apparatus that detects radiation and captures an image.

Figure 2:
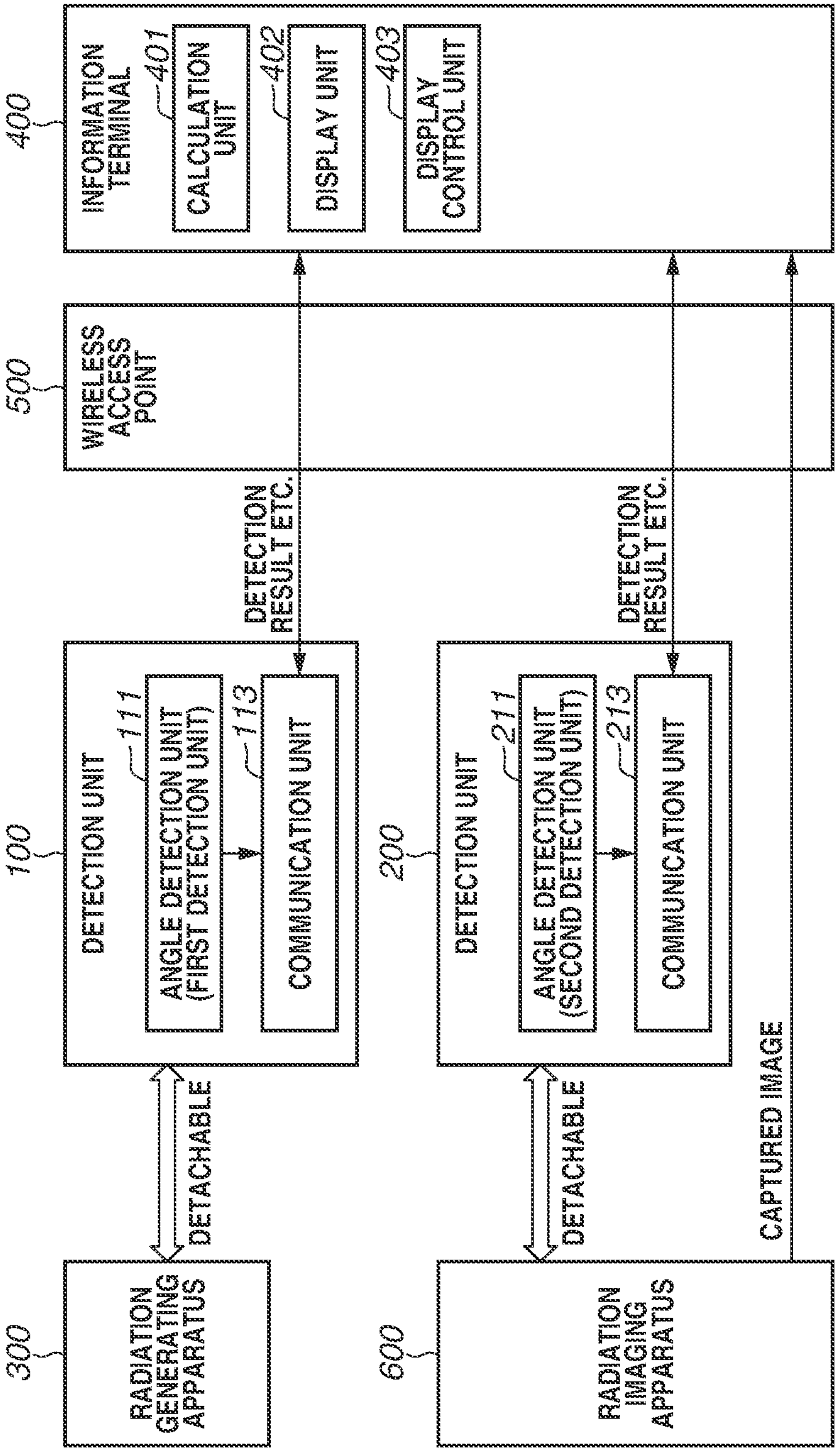
FIG. 2 is a block diagram illustrating the radiation imaging system.

FIG. 2 is a block diagram illustrating the radiation imaging system.

The detection unit 100 is a unit that detects the orientation of the radiation generating apparatus 300. Here, the orientation is an inclination in the three-dimensional space. For example, the orientation is expressed with a combination of a roll angle (θ), a pitch angle (φ), a yaw angle (ψ), or coordinates (x, y, z).

The detection unit 100 can be attached to and detached from the radiation generating apparatus 300. The detection unit 100 includes a communication unit 113 and an angle detection unit 111. The angle detection unit 111 is an example of a first detection unit that detects the orientation of the radiation generating apparatus 300.

The angle detection unit 111 includes a geomagnetic sensor that detects an inclination in an azimuthal direction and an acceleration sensor that detects an inclination in the direction of gravity.

The communication unit 113 has a function of transmitting information, such as a detection result detected by the angle detection unit 111, to external devices (in this embodiment, external devices refer to the information terminal 400 and the radiation imaging apparatus 600) and a function of receiving information on the external devices. A communication scheme for the communication unit 113 can use Wi-Fi® or Bluetooth®. Further, the information may be transmitted or received via the wireless access point 500.

The detection unit 200 is a unit that detects the orientation of the radiation imaging apparatus 600. The detection unit 200 can be attached to and detached from the radiation imaging apparatus 600. The detection unit 200 includes a communication unit 213 and an angle detection unit 211. The angle detection unit 211 is an example of a second detection unit that detects the orientation of the radiation imaging apparatus 600.

The angle detection unit 211 includes a geomagnetic sensor that detects an inclination in an azimuthal direction and an acceleration sensor that detects an inclination in the direction of gravity.

The communication unit 213 has a function of transmitting information, such as a detection result detected by the angle detection unit 211, to the external devices (in this embodiment, external devices refer to the information terminal 400 and the radiation generating apparatus 300) and a function of receiving information on the external devices. A communication scheme for the communication unit 213 can use Wi-Fi® or Bluetooth®. Further, the information may be transmitted or received via the wireless access point 500.

The information terminal 400 is, for example, a personal computer. The information terminal 400 includes a calculation unit 401, such as a central processing unit (CPU) or a field programmable gate array (FPGA), a display unit 402, such as a monitor, and a display control unit 403 that controls display on the display unit 402. The calculation unit 401 is an example of an acquisition unit that acquires relative orientations. The display unit 402 is an example of a display unit that displays instructions to a user and relative orientations. However, the display unit 402 may be separated from the information terminal 400. With the display unit 402 separated, the display unit 402 may be connected to the information terminal 400 in a wired or wireless manner.

Subsequently, an operation of the radiation imaging system according to the present exemplary embodiment will be described with reference to FIGS. 3, 4A, and 4B.

Figure 3:
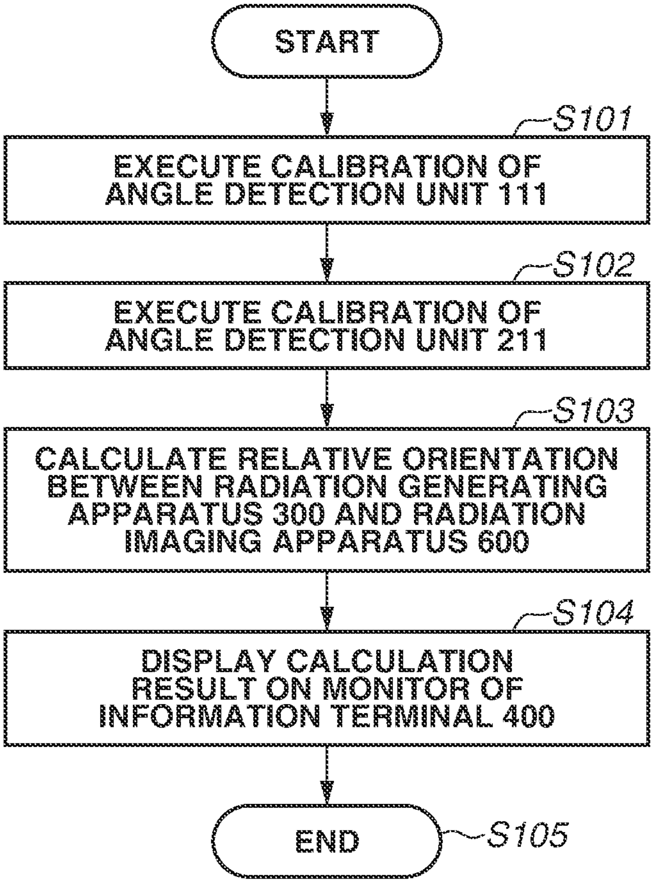
FIG. 3 is a flowchart illustrating an operation of an information terminal.

FIG. 3 is a flowchart illustrating an operation of the information terminal 400 according to the present exemplary embodiment.

If the operation of the radiation imaging system is started, in step S101, the information terminal 400 executes calibration of the angle detection unit 111. When the calibration of the angle detection unit 111 is executed, in step S102, the information terminal 400 executes calibration of the angle detection unit 211.

The calibration is an operation of calculating correction values to reduce the effect of an ambient magnetic field.

Figure 4A:
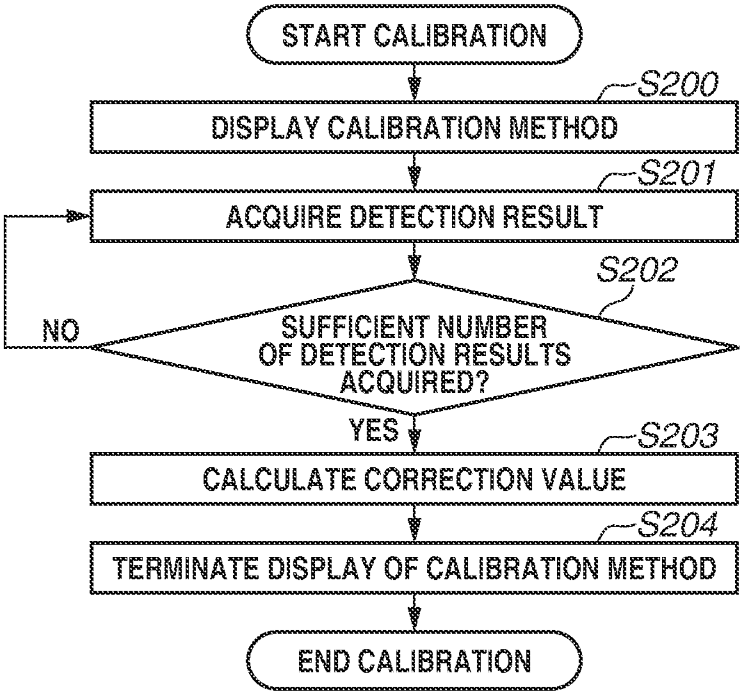
FIG. 4A is a flowchart illustrating an operation of the information terminal.
Figure 4B:
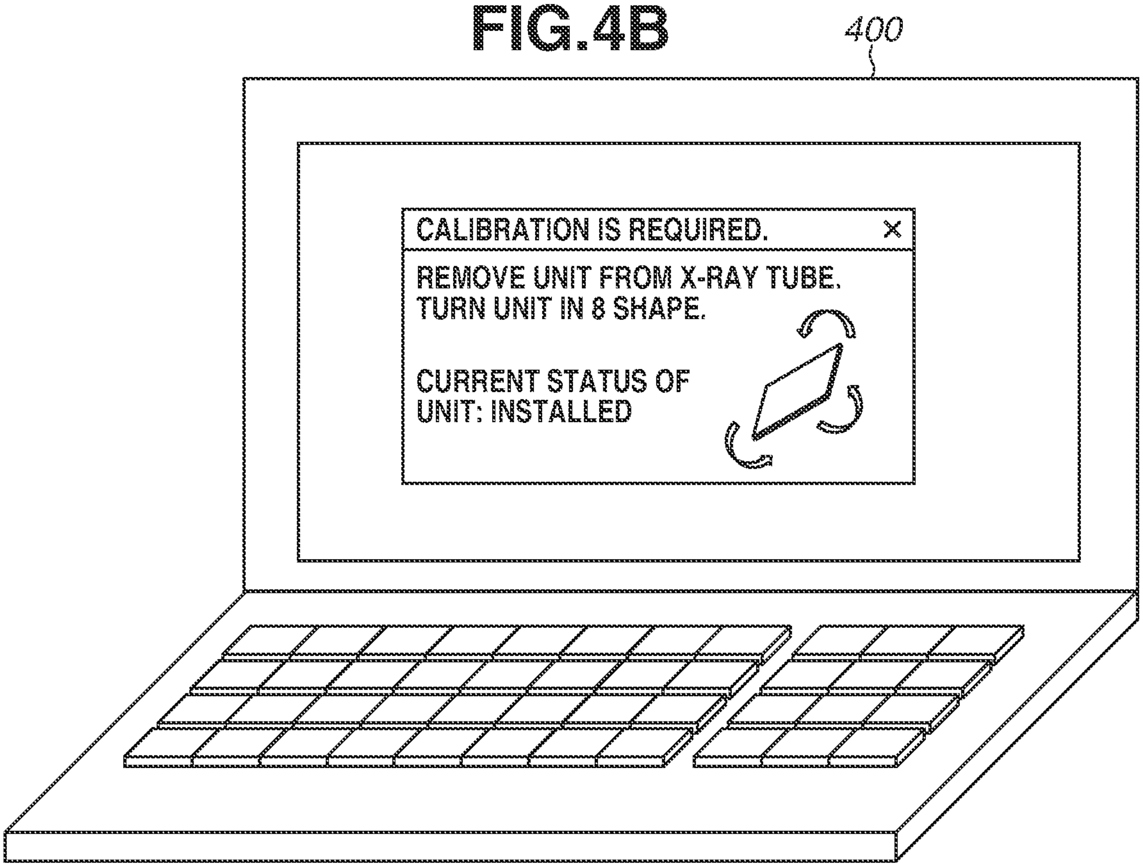
FIG. 4B is a display example.

FIG. 4A is a flowchart illustrating the operation of the information terminal 400 from start to completion of calibration. The operation of the calibration of the angle detection unit 111 will now be described, but the operation of the angle detection unit 211 is also similar.

If the execution of the calibration is started, in step S200, the information terminal 400 displays a calibration method on the display unit 402. Specifically, for example, an instruction to remove the detection unit 100 from the radiation generating apparatus 300, or an instruction to bring the detection unit 100 into a plurality of orientations (for example, turn it in an "8" shape) is displayed. FIG. 4B illustrates a display example. The display example illustrated in FIG. 4B is an example of a result of a display control unit performing control on a display unit. A plurality of orientations acquired by turning the detection unit 100 in "8" shape is an example of a plurality of first orientations and a plurality of second orientations. The motion does not have to be in an "8" shape, and can be any motion that continuously changes the inclination in the three-dimensional space.

Subsequently, in step S201, the information terminal 400 acquires a detection result of the angle detection unit 111. The detection result is transmitted from the angle detection unit 111 via the communication unit 113 and the wireless access point 500 to the information terminal 400.

Subsequently, in step S202, the information terminal 400 determines whether a sufficient number of detection results are acquired to calculate correction values. Here, the correction values refer to a correction value for offset correction (an offset correction value) and a correction value for gain correction (a gain correction value). Details will be described below.

If a sufficient number of detection results have not been acquired yet (NO in step S202), in step S201, the information terminal 400 repeats the operation of acquiring a detection result. The repetition is performed at predetermined time intervals (for example, at intervals of 10 ms). At this time, in addition to the display illustrated in FIG. 4B, a display may be made to emphasize the fact that a sufficient number of detection results has not been acquired.

If a sufficient number of detection results have been acquired (YES in step S202), then in step S203, the information terminal 400 calculates correction values to correct the detection results of the angle detection unit 111.

Specific examples of correction will now be described with reference to FIGS. 5A, 5B, and 6.

Figure 5A:
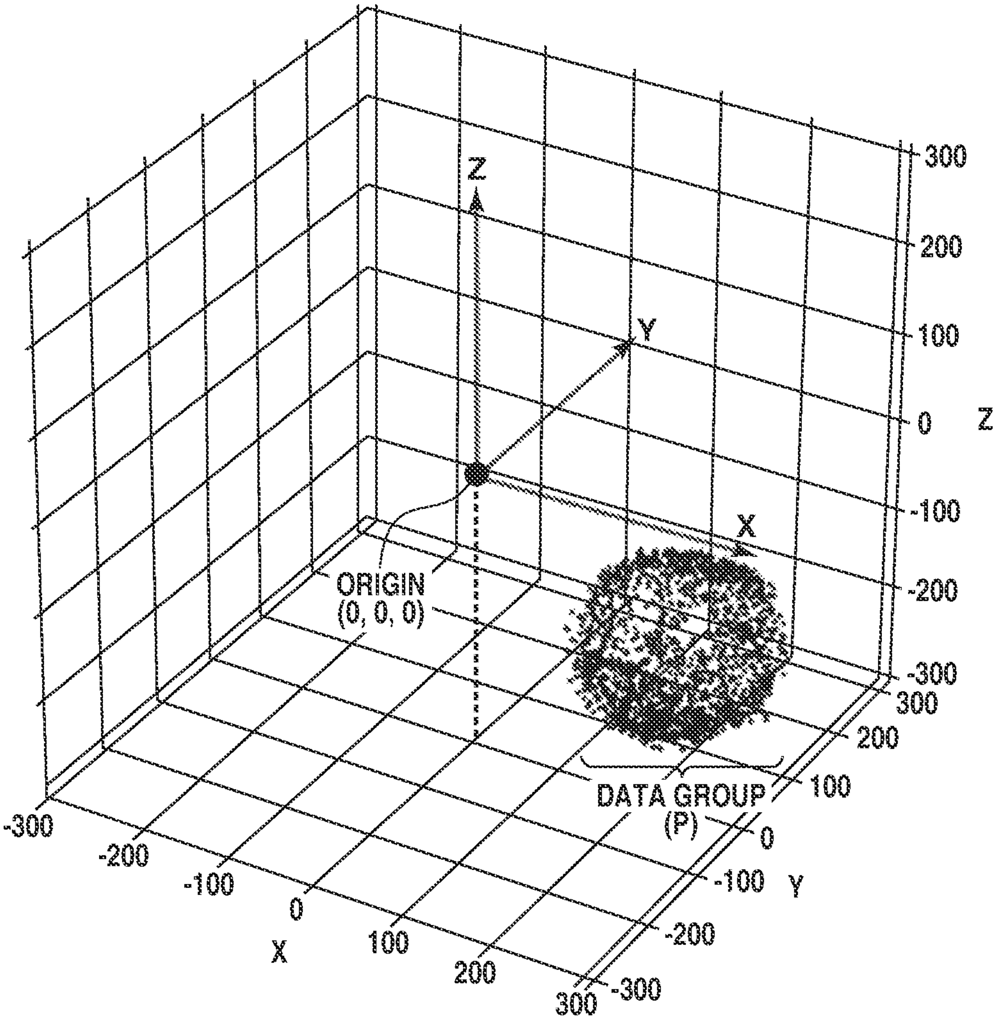
FIGS. 5A and 5B illustrate specific examples of correction.

FIG. 5A illustrates the detection results of the angle detection unit 111 plotted in a right-handed coordinate system. One point included in a data group (P) represents one detection result. If a sufficient number of detection results are acquired, the data group forms a substantial ellipsoid. Here, the data group (P) is an example of a first data group and a second data group.

Figure 5B:
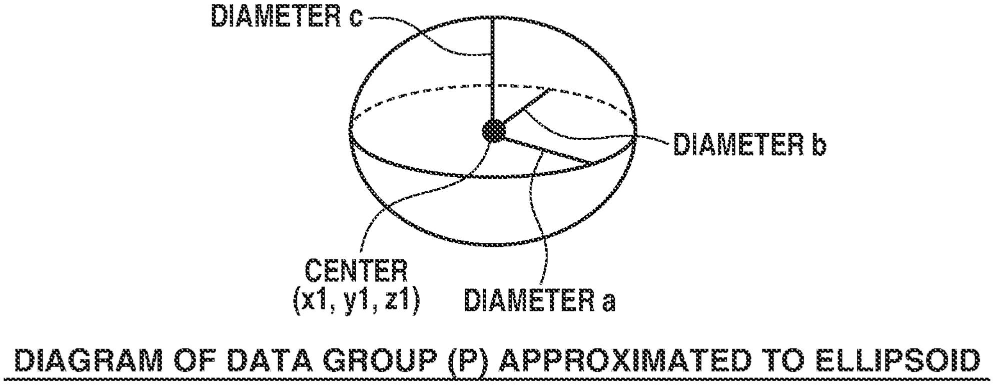

FIG. 5B is a diagram in which the data group (P) is approximated to an ellipsoid. For the approximation, for example, a least-squares method can be used.

If the data group (P) is approximated to an ellipsoid, its center coordinates (x1, y1, z1) and diameters (a, b, c) can be calculated.

If there is no effect of the ambient magnetic field or attenuation of the geomagnetism due to buildings, or other objects, the center coordinates (x1, y1, z1) coincide with the origin. Further, the diameters (a, b, c) have the same value (a=b=c).

However, if there is an effect of the ambient magnetic field, the center coordinates (x1, y1, z1) does not coincide with the origin. Further, the diameters (a, b, c) have different values.

In other words, if there is an effect of the ambient magnetic field, it is necessary to correct the center coordinates and the diameters. Correction to bring the center coordinates closer to the origin is referred to as offset correction. Further, correction to make the diameters (a, b, c) substantially equal values is referred to as gain correction.

In the offset correction, the data group (P) is approximated to an ellipsoid, and its center coordinates (x1, y1, z1) are calculated. The calculated center coordinates themselves indicate deviations from the origin, and thus they are offset correction values. The center coordinates are an example of a first correction value and a second correction value.

In the gain correction, the data group (P) is approximated to an ellipsoid, and its diameters (a, b, c) are calculated. Then, coefficients are calculated that make the diameters b and c equal to the diameter a. These coefficients are regarded as the gain correction values. Specifically, the correction value of the diameter b is a/b. The correction value of the diameter c is a/c. The correction values of the diameters b and c are examples of a first correction value and a second correction value.

Figure 6:
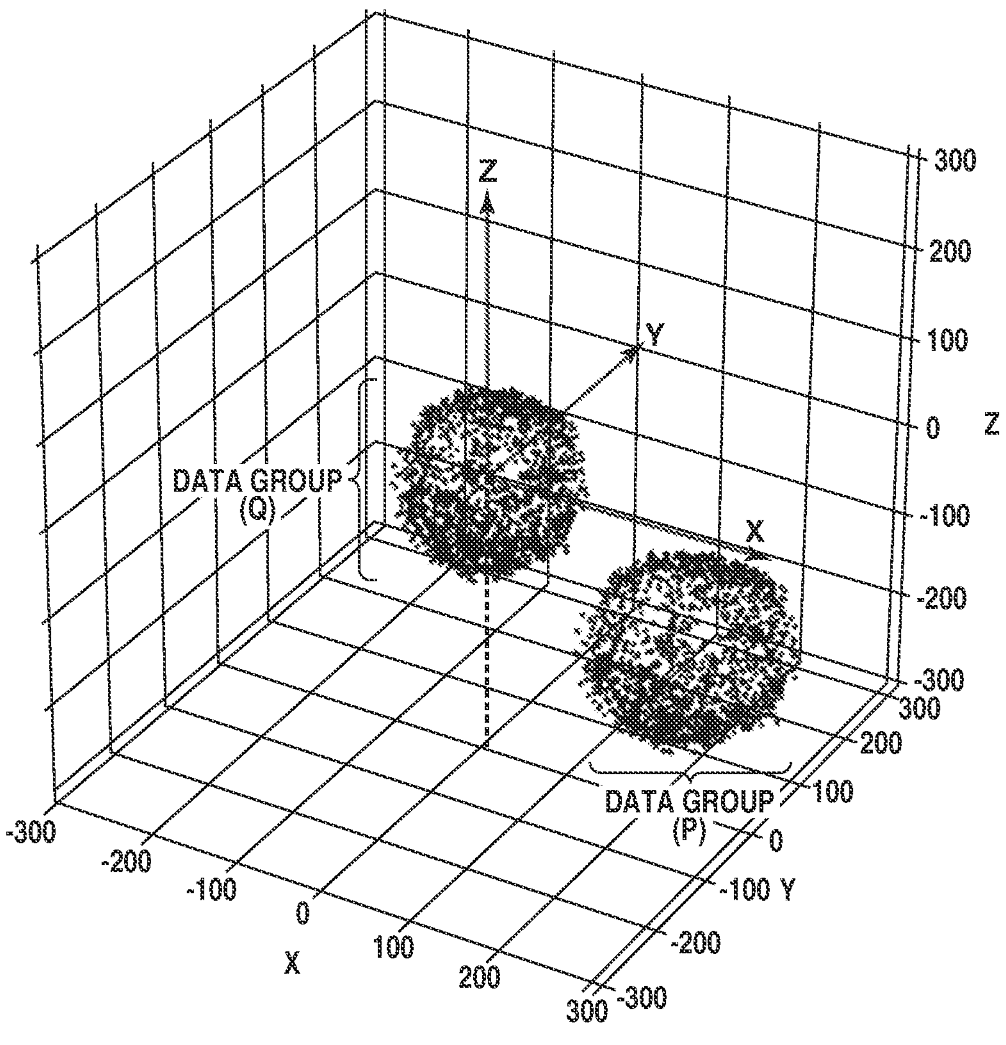
FIG. 6 illustrates a specific example of correction.

FIG. 6 illustrates a data group (Q) that is acquired by performing the offset correction and the gain correction on the data group (P). It can be seen that the center coordinates of the data group (Q) are closer to the origin than those of the data group (P). Further, it can be seen that the form of the data group (Q) is closer to a sphere than that of the data group (P) as the diameters (a, b, c) have approximately the equal values.

If the operation of calculating the correction values is completed, in step S204, the information terminal 400 terminates the display of the calibration method. At this time, the display may be made to emphasize the fact that the calibration is successfully completed.

Through the above-described operations, the calibration of the angle detection unit 111 is completed.

If the calibration of the angle detection unit 111 is completed, then in step S102, the information terminal 400 executes the calibration of the angle detection unit 211. Operations are similar to those of the angle detection unit 111, so that descriptions thereof are omitted.

If the operation in step S101 is completed, the correction values of the angle detection unit 111 are acquired. If the operation in step S102 is completed, the correction values of the angle detection unit 211 are acquired.

Subsequently, in step S103, the information terminal 400 calculates the relative orientation between the radiation generating apparatus 300 and the radiation imaging apparatus 600. The relative orientation is, for example, the inclination of the radiation imaging apparatus 600 with respect to the radiation generating apparatus 300. Specifically, the information terminal 400 calculates the orientation of the radiation generating apparatus 300 by applying the correction values of the angle detection unit 111 acquired in step S101 to the detection results of the angle detection unit 111.

Subsequently, the information terminal 400 calculates the orientation of the radiation imaging apparatus 600 by applying the correction values of the angle detection unit 211 acquired in step S102 to the detection results of the angle detection unit 211. Then, the information terminal 400 calculates the difference between the orientation of the radiation generating apparatus 300 and the orientation of the radiation imaging apparatus 600 and determines the calculation result to be the relative orientation.

Figure 7:
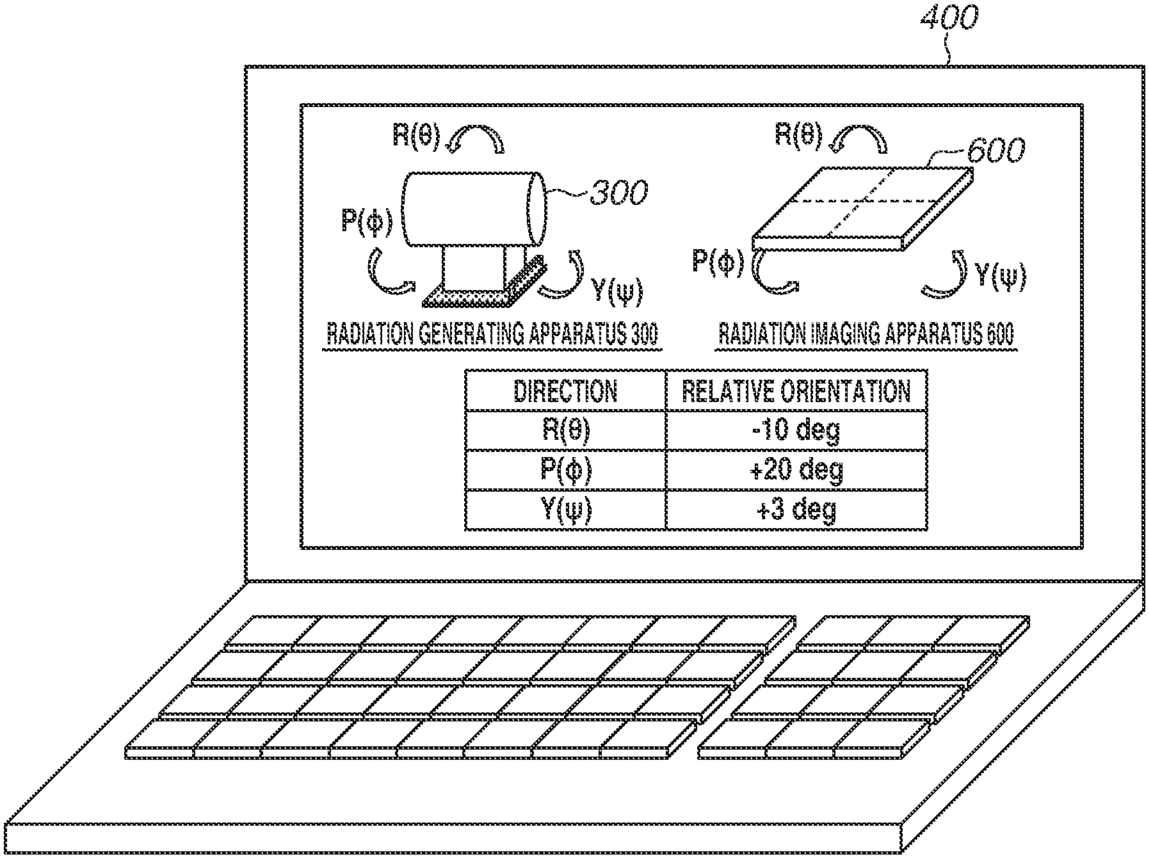
FIG. 7 illustrates a specific example of displaying a relative orientation.

Subsequently, in step S104, the information terminal 400 displays the relative orientation calculated in step S103 on the display unit 402. FIG. 7 illustrates a specific example of a displayed result.

FIG. 7 illustrates an example in which the relative orientation is displayed using a roll angle (θ), a pitch angle (φ), and a yaw angle (ψ). An illustration of the radiation generating apparatus 300 is displayed at the upper left on the screen. An illustration of the radiation imaging apparatus 600 is displayed at the upper right. Further, the relative orientation between the radiation generating apparatus 300 and the radiation imaging apparatus 600 is displayed in the lower part.

Such display allows a user to adjust the inclination of the radiation generating apparatus 300 or the radiation imaging apparatus 600 while checking the display.

The configuration and operations according to the first exemplary embodiment are described above.

According to the first exemplary embodiment, it is described that the information terminal 400 as an acquisition unit performs the calibration and calculation of the relative orientation, but some embodiments are not limited to these operations.

For example, the radiation imaging apparatus 600 may perform the above-described operations. Specifically, the radiation imaging apparatus 600 may receive information regarding the orientation from the radiation generating apparatus 300. Then, a CPU, an FPGA, or the like included in the radiation imaging apparatus 600 may calculate the relative orientation based on the received information. The communication units 113 and 213 are examples of a reception unit that receives information regarding the orientation of an external device.

According to the first exemplary embodiment, it is described that a display is made to prompt a user to remove the detection unit 100 from the radiation generating apparatus 300. However, if it is difficult to remove the detection unit 100, calibration may be performed without removing it.

Further, according to the first exemplary embodiment, it is described that the calibration method and the relative orientation are displayed on the display unit 402 of the information terminal 400, but some embodiments are not limited to this. For example, if the radiation generating apparatus 300 includes the display unit 402, the above-described information may be displayed on the display unit 402 of the radiation generating apparatus 300. If a user adjusts the inclination of the radiation generating apparatus 300, the adjustment is facilitated by displaying the inclination on the display unit 402 of the radiation generating apparatus 300.

Furthermore, according to the present exemplary embodiment, the calibration of the geomagnetic sensor is described in detail, but calibration may be performed on an acceleration sensor. In the calibration of the acceleration sensor, it may be desirable to make the detection unit still once in a plurality of orientations for accuracy improvement.

A second exemplary embodiment will be described. According to the first exemplary embodiment, it is described that both the angle detection units 111 and 211 are set to a plurality of orientations in the calibration.

According to the second exemplary embodiment, it is described that either the angle detection unit 111 or 211 is set to a plurality of orientations in the calibration. According to the second exemplary embodiment, it is only necessary to set either the angle detection unit 111 or 211 to a plurality of orientations, so that time required for the calibration can be reduced. As a result, the configuration provides an effect of further reducing a burden on a user.

A schematic configuration and a block diagram of a radiation imaging system according to the second exemplary embodiment are similar to those according to the first exemplary embodiment, so that descriptions thereof are omitted.

An operation of the radiation imaging system according to the second exemplary embodiment will be described with reference to FIGS. 8A to 8C.

Figure 8A:
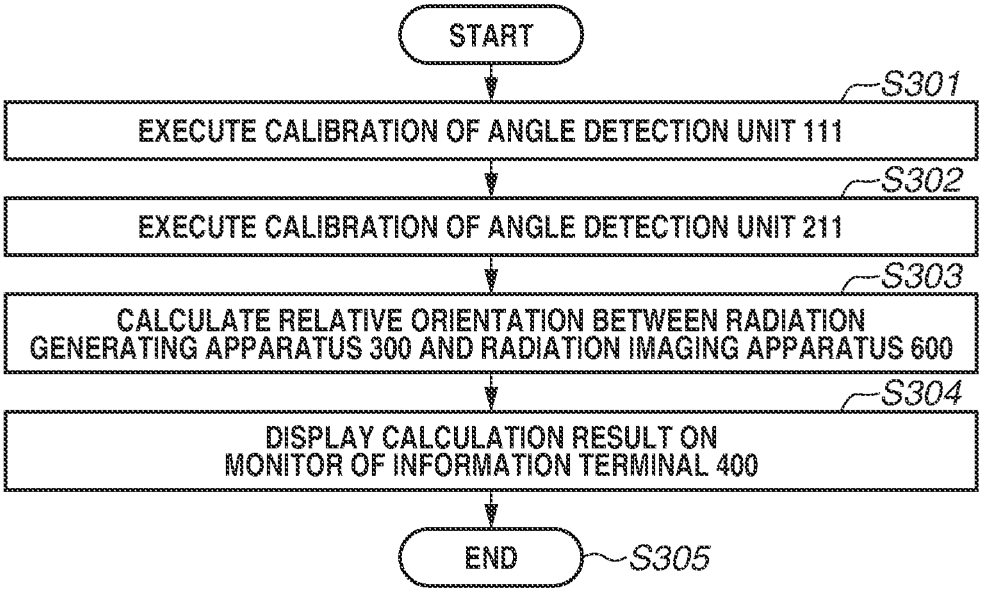
FIGS. 8A to 8C are diagrams illustrating operations of a radiation imaging system according to a second exemplary embodiment.

FIG. 8A is a flowchart illustrating an operation of the information terminal 400 according to the second exemplary embodiment.

If the operation of the radiation imaging system is started, in step S301, the information terminal 400 executes calibration of the angle detection unit 111. Detailed descriptions of the calibration of the angle detection unit 111 are omitted because they are similar to those according to the first exemplary embodiment.

If the calibration of the angle detection unit 111 is completed, then in step S302, the information terminal 400 executes the calibration of the angle detection unit 211.

Figure 8B:
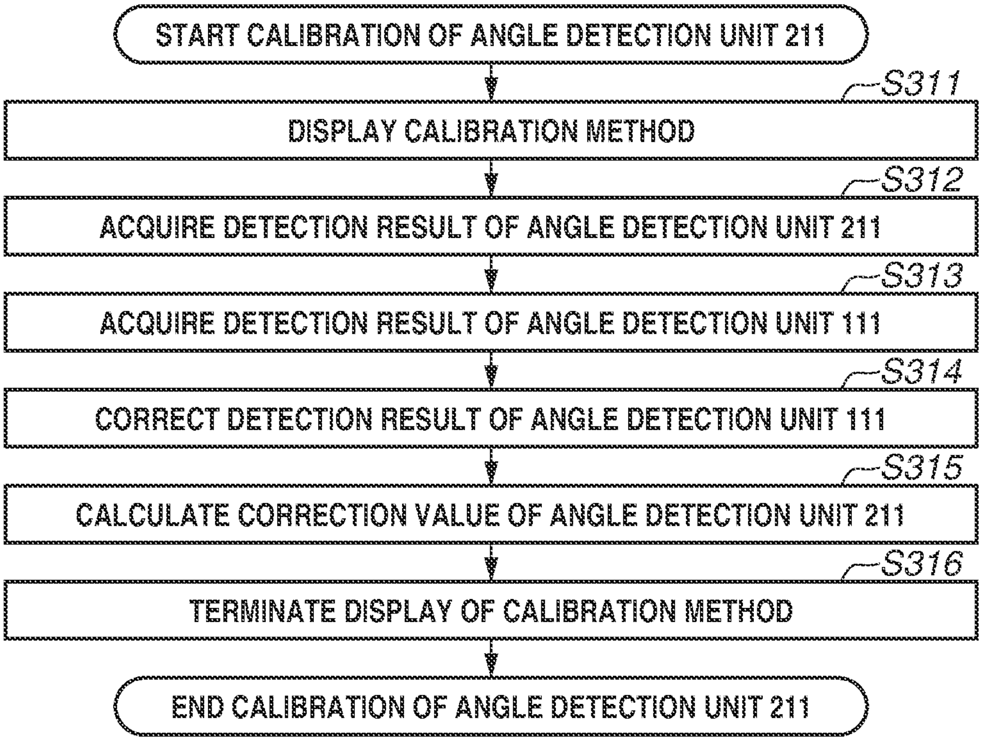
Figure 8C:
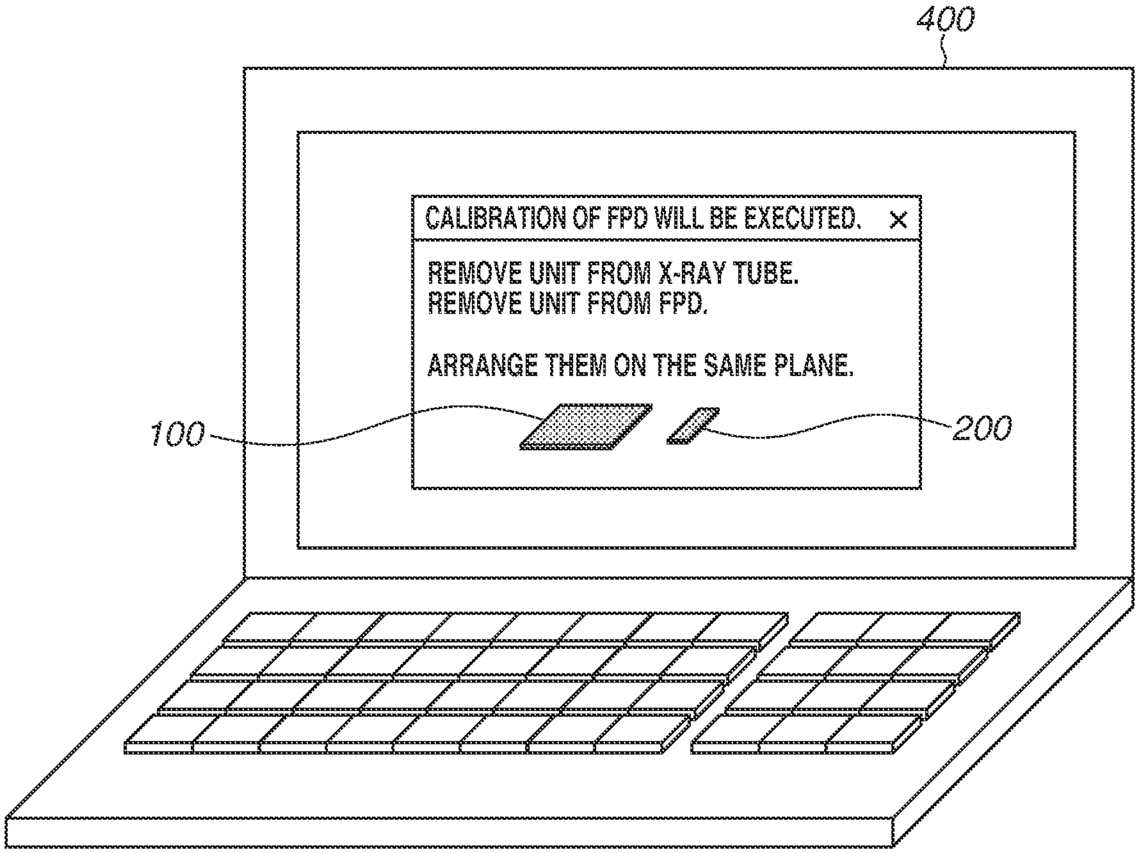

FIG. 8B is a flowchart illustrating the operation of the information terminal 400 from start to completion of the calibration of the angle detection unit 211.

If execution of the calibration is started, in step S311, the information terminal 400 displays a calibration method on the display unit 402. Specifically, for example, the information terminal 400 performs a display prompting a user to remove the detection unit 100 from the radiation generating apparatus 300, a display prompting the user to remove the detection unit 200 from the radiation imaging apparatus 600, and a display prompting the user to set the detection units 100 and 200 to a predetermined relative orientation. Here, the predetermined relative orientation is, for example, a relative orientation if the detection units 100 and 200 are arranged on the same plane. FIG. 8C illustrates a display example. The arrangement does not have to be made on the same plane as long as the relative orientation is known in advance. For example, the detection units 100 and 200 may be arranged substantially vertically.

Subsequently, in step S312, the information terminal 400 acquires the detection results of the angle detection unit 211.

Subsequently, in step S313, the information terminal 400 acquires the detection results of the angle detection unit 111.

Subsequently, in step S314, the information terminal 400 corrects the detection results of the angle detection unit 111 acquired in step S313. Specifically, the information terminal 400 applies the correction values (the offset correction value and the gain correction value) acquired in step S301 to the detection results acquired in step S313. The corrected detection results of the angle detection unit 111 are expressed as the detection results (after correction) of the angle detection unit 111.

Subsequently, in step S315, the information terminal 400 calculates the correction values of the angle detection unit 211. Specifically, the information terminal 400 compares the detection results of the angle detection unit 211 acquired in step S312 with the detection results (after correction) of the angle detection unit 111 acquired in step S314 and determines the difference therebetween to be the correction values.

This is because the detection units 100 and 200 are arranged on the same plane in step S311, so that the detection results of the angle detection unit 211 are originally to be equivalent to the detection results (after correction) of the angle detection unit 111.

If the operation of calculating the correction values of the angle detection unit 211 is completed, in step S316, the information terminal 400 terminates the display of the calibration method. At this time, a display may be made to emphasize the fact that the calibration is successfully completed.

Through the above-described operations, the calibration of the angle detection unit 211 is completed.

If the calibration of the angle detection unit 211 is completed, in step S303, the information terminal 400 calculates the relative orientation between the radiation generating apparatus 300 and the radiation imaging apparatus 600, and then in step S304, displays the calculated relative orientation on the display unit 402. These operations are similar to those according to the first exemplary embodiment, so that descriptions thereof are omitted.

The configuration and operations according to the second exemplary embodiment are described above.

Here, according to the second exemplary embodiment, it is described that, between the angle detection units 111 and 211, only the angle detection unit 111 is set to a plurality of orientations, but the same effect can be achieved if only the angle detection unit 211 is set to a plurality of orientations.

Here, according to the first and the second exemplary embodiments, an ultrasonic generating apparatus may be used in addition to the radiation generating apparatus 300. Further, the radiation imaging apparatus 600 may be an ultrasonic imaging apparatus.

Other Exemplary Embodiments

The techniques in the present disclosure can also be realized by executing the following processing. In other words, the techniques according to the present disclosure can also be realized by processing in which software (e.g., a program) for carrying out one or more functions of the above-described exemplary embodiments is supplied to a system or an apparatus via a network or a storage medium and a computer (or a CPU or a micro processing unit (MPU)) of the system or the apparatus reads and executes the software. The computer may include one or a plurality of processors or other circuits, and a plurality of separate computers, or a network of a plurality of separate processors or other circuits can be included in order to read and execute computer-executable instructions. At this time, the processor or other circuit may include a CPU, an MPU, a graphics processing unit (GPU), an application specific integrated circuit (ASIC), or an FPGA. Further, the processor or other circuit may also include a digital signal processor (DSP), a data flow processor (DFP), or a neural processing unit (NPU).

The descriptions according to the present exemplary embodiments include the following configuration, method, and program.

(Configuration 1)

An information processing apparatus comprising a correction unit configured to, based on a data group that is acquired in a state in which a detection unit configured to detect an orientation is not attached to a radiation imaging apparatus and is acquired by the detection unit detecting a plurality of orientations, correct an orientation that is detected by the detection unit after the plurality of orientations is detected and is acquired in a state in which the detection unit is attached to the radiation imaging apparatus.

(Configuration 2)

The information processing apparatus according to the configuration 1,

- wherein the detection unit includes a geomagnetic sensor, and
- wherein the data group is a data group regarding an azimuth acquired by the geomagnetic sensor detecting the plurality of orientations.

(Configuration 3)

The information processing apparatus according to the configuration 1, wherein the correction unit corrects an orientation detected by the detection unit after the plurality of orientations is detected based on correction values that are acquired by approximating a form of the data group to an ellipsoid.

(Configuration 4)

The information processing apparatus according to any one of the configurations 1 to 3, wherein the correction unit corrects an orientation detected by the detection unit after the plurality of orientations is detected based on the correction values that are acquired by approximating the form of the data group to an ellipsoid, the correction values being used for correcting center coordinates and diameters of the ellipsoid.

(Configuration 5)

The information processing apparatus according to the configuration 4, wherein the correction values include an offset correction value for correcting a deviation of the center coordinates of the ellipsoid with respect to origin coordinates and a gain correction value for correcting the diameters of the ellipsoid to be substantially equal.

(Configuration 6)

The information processing apparatus according to any one of the configurations 1 to 5, further comprising a display control unit configured to perform control to display an attachment/detachment state between the detection unit and the radiation imaging apparatus and to perform control to display an instruction prompting a user to attach the detection unit to the radiation imaging apparatus in a case where the detection unit is not attached to the radiation imaging apparatus after the plurality of orientations is detected.

(Configuration 7)

A radiation imaging system comprising:

a radiation imaging apparatus configured to detect radiation and capture an image; and the information processing apparatus according to any one of the configurations 1 to 6 that is communicably connected to the radiation imaging apparatus.

(Configuration 8)

A radiation imaging system comprising:

a radiation generating apparatus configured to generate radiation; and the information processing apparatus according to any one of the configurations 1 to 7 that is communicably connected to the radiation generating apparatus, wherein the correction unit acquires a relative orientation between the radiation generating apparatus and the radiation imaging apparatus using information regarding a corrected orientation and an orientation of the radiation generating apparatus.

(Configuration 9)

The radiation imaging system according to the configuration 8 further comprising a display control unit configured to perform control to display the relative orientation on a display unit.

(Configuration 10)

A radiation imaging system comprising:

a radiation generating apparatus configured to generate radiation;

a radiation imaging apparatus configured to detect the radiation and capture an image;

a first detection unit configured to detect an orientation of the radiation generating apparatus;

a second detection unit configured to detect an orientation of the radiation imaging apparatus; and a correction unit configured to correct, based on a first data group acquired by the first detection unit detecting a plurality of first orientations, a first orientation detected by the first detection unit after the plurality of first orientations is detected, to correct, based on a second data group acquired by the second detection unit detecting a plurality of second orientations, a second orientation detected by the second detection unit after the plurality of second orientations is detected, and to acquire a relative orientation between the radiation generating apparatus and the radiation imaging apparatus using the corrected first orientation and the corrected second orientation.

(Method 1)

A method for processing information, the method comprising, based on a data group that is acquired in a state in which a detection unit configured to detect an orientation is not attached to a radiation imaging apparatus and is acquired by the detection unit detecting a plurality of orientations, correcting an orientation that is detected by the detection unit after the plurality of orientations is detected and is acquired in a state in which the detection unit is attached to the radiation imaging apparatus.

(Storage Medium 1)

A storage medium storing a program for causing a computer to execute the method for processing information according to the method 1.

According to the present disclosure, it is possible to improve detection accuracy of an inclination of a radiation imaging apparatus with respect to a radiation generating apparatus.

Embodiment(s) of the present disclosure can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc™ (BD)), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2023-050410, which was filed on Mar. 27, 2023 and which is hereby incorporated by reference herein in its entirety.

What is claimed is:

1. An information processing apparatus comprising:

one or more memories; and one or more processors, wherein the one or more memories and the one or more processors are configured to, based on a data group that is acquired in a state in which a detection unit configured to detect an orientation of the detection unit is not attached to a flat panel detector and is acquired by the detection unit detecting a plurality of orientations of the detection unit, correct an orientation of the detection unit that is detected by the detection unit after the plurality of orientations is detected and is acquired in a state in which the detection unit is attached to the flat panel detector.

2. The information processing apparatus according to claim 1, wherein the detection unit includes a geomagnetic sensor, and wherein the data group is a data group regarding an azimuth acquired by the geomagnetic sensor detecting the plurality of orientations.

3. The information processing apparatus according to claim 1, wherein the one or more memories and the one or more processors are further configured to correct an orientation detected by the detection unit after the plurality of orientations is detected based on a correction value that is acquired by approximating a form of the data group to an ellipsoid.

4. The information processing apparatus according to claim 1, wherein the one or more memories and the one or more processors are further configured to correct an orientation detected by the detection unit after the plurality of orientations is detected based on correction values that are acquired by approximating a form of the data group to an ellipsoid, the correction values being used for correcting center coordinates and diameters of the ellipsoid.

5. The information processing apparatus according to claim 4, wherein the correction values include an offset correction value for correcting a deviation of the center coordinates of the ellipsoid with respect to origin coordinates and a gain correction value for correcting the diameters of the ellipsoid to be substantially equal.

6. The information processing apparatus according to claim 1, wherein the one or more memories and the one or more processors are further configured to:

perform control to display an attachment/detachment state between the detection unit and the flat panel detector; and perform control to display an instruction prompting a user to attach the detection unit to the flat panel detector in a case where the detection unit is not attached to the flat panel detector after the plurality of orientations is detected.

7. A radiation imaging system comprising:

the flat panel detector configured to detect radiation and capture an image; and the information processing apparatus according to claim 1, wherein the information processing apparatus is communicably connected to the flat panel detector.

8. A radiation imaging system comprising:

a radiation generating apparatus configured to generate radiation; and the information processing apparatus according to claim 1, wherein the information processing apparatus is communicably connected to the radiation generating apparatus, wherein the one or more memories and the one or more processors are further configured to acquire a relative orientation between the radiation generating apparatus and the radiation imaging apparatus using information regarding a corrected orientation and an orientation of the radiation generating apparatus.

9. The radiation imaging system according to claim 8, wherein the one or more memories and the one or more processors are further configured to perform control to display the relative orientation on a display unit.

10. A radiation imaging system comprising:

a radiation generating apparatus configured to generate radiation;

a radiation imaging apparatus configured to detect the radiation and capture an image;

a first detection unit configured to detect an orientation of the radiation generating apparatus;

a second detection unit configured to detect an orientation of the radiation imaging apparatus;

one or more memories; and one or more processors, wherein the one or more memories and the one or more processors are configured to:

correct, based on a first data group acquired by the first detection unit detecting a plurality of first orientations, a first orientation detected by the first detection unit after the plurality of first orientations is detected, correct, based on a second data group acquired by the second detection unit detecting a plurality of second orientations, a second orientation detected by the second detection unit after the plurality of second orientations is detected, and acquire a relative orientation between the radiation generating apparatus and the radiation imaging apparatus using the corrected first orientation and the corrected second orientation.

11. A method for processing information, the method comprising:

based on a data group that is acquired in a state in which a detection unit configured to detect an orientation of the detection unit is not attached to a flat panel detector and is acquired by the detection unit detecting a plurality of orientations of the detection unit, correcting an orientation of the detection unit that is detected by the detection unit after the plurality of orientations is detected and is acquired in a state in which the detection unit is attached to the flat panel detector.

12. A storage medium storing a program for causing a computer to execute the method according to claim 11.

* * * * *